(12) United States Patent
Markert et al.

(10) Patent No.: US 6,313,354 B1
(45) Date of Patent: Nov. 6, 2001

(54) METHOD FOR PRODUCING AROMATIC ALDEHYDES

(75) Inventors: Thomas Markert, Monheim; Ralph Nemitz, Juechen, both of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/402,213

(22) PCT Filed: Mar. 27, 1998

(86) PCT No.: PCT/EP98/01820

§ 371 Date: Sep. 30, 1999

§ 102(e) Date: Sep. 30, 1999

(87) PCT Pub. No.: WO98/45237

PCT Pub. Date: Oct. 15, 1998

(30) Foreign Application Priority Data

Apr. 5, 1997 (DE) ............................................. 197 14 042

(51) Int. Cl.⁷ .................................................. C07C 45/00
(52) U.S. Cl. ............................................. 568/426; 568/425
(58) Field of Search .................................. 568/424, 425, 568/426, 433

(56) References Cited

U.S. PATENT DOCUMENTS

| 4,113,781 | 9/1978 | Aquila et al. ........................ 260/599 |
| 4,556,743 | 12/1985 | McKenna et al. .................... 568/433 |
| 4,614,611 | 9/1986 | Sprecker .......................... 252/528 R |

FOREIGN PATENT DOCUMENTS

| 23 40 812 | 2/1975 | (DE) . |
| 0 052 775 | 6/1982 | (EP) . |

OTHER PUBLICATIONS

Tetrahedron Letters, 35(31), pp. 5595–5598, 1994.*
Chem. Abstracts, vol. 99, No. 21, abstract No. 17309d, p. 580 (1983).
Maslo. Zhir. Prom. St., vol. 7, pp. 32–34 (1983).
Journal of Amer. Chem. Soc., vol. 78, pp. 3209–3210 (1956).
Houben–Weyl, Methoden der organischen Chemie, 4$^{th}$ Ed., vol. VII, Part 1, pp. 112 and 115–117, 1954.
J.Org. Chem., vol. 43, No. 10, pp. 2068–2069 (1983).
Synthetic Communications, vol. 27, No. 1, XP002073790, pp. 11–15 (1997).

* cited by examiner

*Primary Examiner*—Sreeni Padmanabhan
(74) *Attorney, Agent, or Firm*—John E. Drach; Henry E. Millson, Jr.

(57) ABSTRACT

A process for the preparation of aromatic aldehydes comprising the steps of condensing a phenone ketal with a vinyl ether in the presence of a Lewis acid, subjecting the resulting acetal to acidic hydrolysis to form the corresponding α,β-unsaturated aldehyde, and optionally hydrogenating the C=C double bond of said unsaturated aldehyde.

9 Claims, No Drawings

METHOD FOR PRODUCING AROMATIC ALDEHYDES

This is the U.S. National Stage Application of PCT/EP98/01820 filed Mar. 27, 1998.

FIELD OF THE INVENTION

This invention relates to a process for the production of aromatic aldehydes from phenone ketals having a special structure. In this process, the phenone ketal is first condensed with a vinyl ether in the presence of Lewis acids, the acetal formed is subjected to acidic hydrolysis to form the corresponding α,β-unsaturated aldehyde and, if desired, the C=C double bond of this aldehyde is selectively hydrogenated in the usual way.

BACKGROUND OF THE INVENTION

Judging by demand, many natural perfumes are available in totally inadequate quantities. For example, 5,000 kg of rose blossoms are required to obtain 1 kg of rose oil. The consequences are extremely limited annual world production and a high price. Accordingly, it is clear that there is a constant need in the perfume industry for new perfumes with interesting fragrance notes in order to extend the range of naturally available perfumes, to make the necessary adaptations to changing fashion trends and to be able to meet the steadily increasing demand for odor enhancers for products of everyday use, such as cosmetics and cleaners.

Accordingly, it is clear that there is a constant need in the perfume industry for new perfumes with interesting fragrance notes in order to extend the range of naturally available perfumes, to make the necessary adaptations to changing fashion trends and to be able to meet the steadily increasing demand for odor enhancers for products of everyday use, such as cosmetics and cleaners.

In addition, there is generally a constant need for synthetic perfumes which can be favorably produced in a consistent quality and which have desirable olfactory properties, i.e. pleasant, near-natural and qualitatively new odor profiles of adequate intensity, and which are capable of advantageously influencing the fragrance of cosmetic and consumer products.

In this connection, the purity and hence the odor profile of synthetic perfumes are having to meet increasingly more stringent requirements. This means that the development of processes by which synthetic perfumes with improved purity and an improved odor characteristic can be obtained are acquiring increasing significance. These improved production processes generally have the additional advantage that the perfumes thus produced also show more favorable ecotoxicological properties by virtue of their greater purity.

At present, there is a particular demand among perfume experts for perfumes which have a pronounced musk odor characteristic.

4-tert.butylvinyl propionaldehyde and its α-methyl analog are known are possible perfume components from U.S. Pat. No. 626,548. According to U.S. Pat. No. 626,548, they can be obtained by hydroformylating α-methyl styrene with hydrogen and carbon monoxide in the presence of rhodium or cobalt catalysts.

DESCRIPTION OF THE INVENTION

The problem addressed by the present invention was to provide an improved process for the production of aromatic aldehydes having perfume properties.

The present invention relates to a process for the production of aromatic aldehydes having perfume properties which correspond to general formula (I):

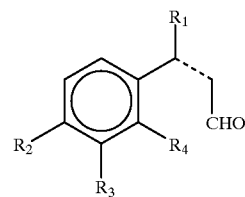

(I)

where $R_1$ is a methyl, ethyl or propyl group, $R_2$ is a methyl, ethyl, isopropyl, tert.butyl or methoxy group, $R_3$ is hydrogen or a methoxy group and $R_4$ is hydrogen or a methyl group and where the chain line represents a C—C single bond or C=C double bond which may have an E or Z configuration, characterized in that
a) a phenone ketal corresponding to general formula (II):

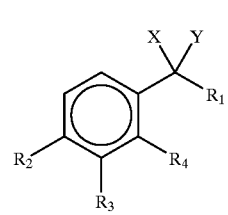

(II)

where X and Y independently of one another represent methoxy, ethoxy, propoxy or butoxy groups and $R_1$ is a methyl, ethyl or propyl group, $R_2$ is a methyl, ethyl, isopropyl, tert.butyl or methoxy group, $R_3$ is hydrogen or a methoxy group and $R_4$ is hydrogen or a methyl group, is added onto a vinyl ether corresponding to general formula (III):

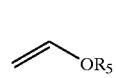

(III)

where $R_5$ is an alkyl group containing 1 to 4 carbon atoms, in the presence of Lewis acids,
b) the acetal formed is subjected to acidic hydrolysis to form the corresponding α,β-unsaturated aldehyde and
c) if desired, the C=C double bond of this aldehyde is selectively hydrogenated in the usual way.

Zinc chloride is preferably used as the Lewis acid catalyst in step a).

The compounds corresponding to formula (I) may be produced either in pure form or in the form of mixtures with one another by the process according to the invention.

The aromatic aldehydes (I) produced by the process according to the invention are distinguished from corresponding compounds produced by hydroformylation of corresponding styrenes in accordance with the prior art by improved purity and an improved odor characteristic.

In another embodiment, therefore, the invention relates to the use of the aromatic aldehydes (I) produced by the process according to the invention as perfumes.

In one preferred embodiment of the invention, the hydrogenation step c) is compulsory.

The individual steps of the reaction sequence a) to c) of the process according to the invention are known per se from the literature.

For example, the addition of ketals onto vinyl ether in the presence of boron trifluoride etherate is known from Houben-Weyl, Methoden der organischen Chemie, 4th Edition, Vol. VII, Part 1, pages 112 and 115–117 (Stuttgart 1954).

J. Org. Chem., Vol. 43, No. 10, 1978 pages 2068–2069 describes a synthesis route for the production of pheromonene in which 1,1-dioxyethyl-3,3-dimethyl cyclohexane is converted into the corresponding acetal by reaction with ethyl vinyl ether in the presence of zinc chloride and the acetal obtained is hydrolyzed with acetic acid/sodium acetate/water to form the corresponding isomeric unsaturated aldehydes.

The present invention also relates to the new substance 3-(2,4-dimethylphenyl)-butanal.

The following Examples are intended to illustrate the invention without limiting it in any way.

EXAMPLES

Precursor 1: 1-(1,1-diethoxyethyl)-2,4-dimethyl benzene

Materials
1) 97.3 g (0.66 mol) 2,4-dimethyl acetophenone (Fluka)
2) 117.3 g (0.79 mol) triethyl orthoformate (Fluka)
3) 123.7 mg potassium hydrogen sulfate (Merck)
4) 600 ml ethanol, water-free (technical quality)

Method

Substances 1) to 4) were introduced into a 1-liter three-necked flask and stirred for 78 hours at 20° C. in the absence of moisture (drying tube filled with silica gel) while dry nitrogen (ca. 2 l/h) was passed through. Thereafter no more educt could be detected in the mixture by GLC. For working up, the catalyst was neutralized with 2 ml of sodium methylate solution (30% in methanol) and the mixture was stirred for 15 minutes. The ethanol was then removed in a rotary evaporator and the remaining 150.9 g of light-brown residue was used for distillation in a 15 cm packed column (Braunschweig coils). 133.5 g of main runnings with a boiling point of 73–75° C./0.1 mbar were obtained. The gas chromatographic purity was 94.6%.

Odor Description: Musk, Anthranilate, Sulfur Rubber Note

Precursor 2: 2,4-dimethyl-1-(1,3,3-triethoxy-1-methylpropyl)-benzene

Materials
1) 127.6 g (0.57 mol) 1-(1,1-diethoxyethyl2,4-dimethyl benzene prepared as described above under "precursor 1"
2) 44.9 ml $ZnCl_2$ solution (10% in ethyl acetate)
3) 59.5 ml (0.65 mol) ethylvinyl ether (Acros)

Method

The ketal 1) and the zinc(II) chloride solution were heated with stirring to 40–45° C. in a 1-liter three-necked flask purged with dry nitrogen. The ethylvinyl ether was continuously added dropwise over a period of 1 hour at ca. 50° C., followed by stirring for another ca. 15 hours at 50° C. Thereafter the starting ketal had completely reacted. For working up, the reaction mixture was diluted with diethyl ether and washed with quantities of ca. 150 ml of 5% sodium hydroxide and water, the organic phases were dried over sodium sulfate and concentrated. The remaining 146.7 g of yellow liquid were used for distillation in a 15 cm packed column. 90.4 g of main runnings with a boiling point of 101–105° C. and a gas chromatographic purity of 96.6% were obtained in this purification step.

Odor Description: Flowery, Sweet, Cinnamon Note

Example 1

3-(2,4-dimethylphenyl)-but-2-enal

Materials
1) 70.5 g (0.25 mol) 2,4-dimethyl-1-(1,3,3-triethoxy-1-methylpropyl)-benzene prepared as described above under "precursor 2"
2) 342.9 g (5.69 mol) acetic acid, 99% (Riedel de Haen)
3) 35.7 g (0.44 mol) sodium acetate (Merck)
4) 24.1 g distilled water Method Components 1) to 4) were introduced into a 1 liter three-necked flask equipped with a stirrer, thermometer and reflux condenser and stirred for 3 hours at 90 to 95° C. The heating bath was then removed and the temperature was allowed to return overnight to room temperature with stirring. ca. 200 ml of diethyl ether were added and the mixture was poured onto ca. 500 g of ice. The now vigorously foaming mixture was neutralized while stirring with solid sodium bicarbonate in a 2 liter glass beaker. The organic phase was removed, washed with ca. 150 ml of water, dried over sulfate and concentrated. 45.3% of a dark brown residue were used for distillation in a 30 cm long packed column. The main runnings consisted of 29.4 g of a pale yellowish liquid with a boiling of 76° C./0.08 mbar and a gas chromatographic purity of 95.3%.

Odor Description: Flowery, Cedarwood, Pungently Aldehydic

Example 2

3-(2,4-dimethylpheny)-butanal

Materials
1) 19.5 g (0.11 mol) 3-(2,4-dimethylphenyl)-but-2-enal prepared as in Example 1
2) 0.2 g 5% Pd/C (RCh-Katalysator 50/8, Hoechst)
3) 200 ml ethanol (technical quality)

Method

The components were introduced together into a steel autoclave and stirred for 5 hours at 70° C. under a pressure of 20 bar hydrogen. No significant reduction in pressure was observed. After the catalyst had been filtered off and the ethanolic solution concentrated, 18.5 g of a colorless liquid were used for distillation in a 30 cm packed column. 10.3 g of main runnings distilled over at a boiling point of 62 to 63° C. The gas chromatographic purity was 93%.

Odor Description: Flowery, Privet, Anthralinate, Nitromusk Note

What is claimed is:

1. A process for the preparation of aromatic aldehydes having perfume properties wherein the aromatic aldehydes correspond to formula (I):

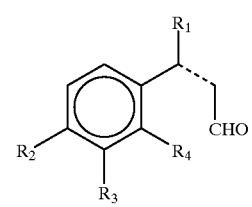

(I)

where $R_1$ is a methyl, ethyl or propyl group, $R_2$ is a methyl, ethyl, isopropyl, tert.butyl or methoxy group, $R_3$ is hydrogen or a methoxy group, $R_4$ is hydrogen or a methyl group, and where the dotted line represents a C—C single bond or a C=C double bond which can have the E or Z configuration, comprising the steps of A) reacting a phenone ketal corresponding to formula (II):

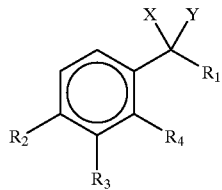

(II)

where X and Y independently of one another represent methoxy, ethoxy, propoxy or butoxy groups and $R_1$ is a methyl, ethyl or propyl group, $R_2$ is a methyl, ethyl, isopropyl, tert.butyl or methoxy group, $R_3$ is hydrogen or a methoxy group and $R_4$ is hydrogen or a methyl group, with a vinyl ether corresponding to formula (III):

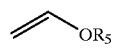

(III)

where $R_5$ is an alkyl group containing 1 to 4 carbon atoms, in the presence of a Lewis acid to form an acetal;

B) subjecting the acetal to acid hydrolysis to form the corresponding α,β-unsaturated aldehyde of formula I; and, optionally, C) selectively hydrogenating the C=C double bond of the aldehyde.

2. The process of claim 1 wherein in step A) the Lewis acid is zinc chloride.

3. The process of claim 1 wherein in the phenone ketal of formula II, both X and Y are ethoxy groups.

4. The process of claim 2 wherein in the phenone ketal of formula II, both X and Y are ethoxy groups.

5. The process of claim 1 wherein in step A) the vinyl ether of formula III is ethylvinyl ether.

6. The process of claim 1 wherein in step B) the acid used to acid hydrolyze the acetal is acetic acid.

7. The process of claim 1 wherein the aromatic aldehyde of formula I produced by the process of steps A) and B) is 3-(2,4-dimethylphenyl)-but-2-enal.

8. The process of claim 7 wherein step C) is carried out to produce 3-(2,4-dimethylphenyl)-butanal.

9. The process of claim 1 wherein in step A) the phenone ketal of formula II is 1-(1,1-diethoxyethyl)-2,4-dimethyl benzene, and the vinyl ether of formula III is ethylvinyl ether.

* * * * *